United States Patent [19]
Sawyer et al.

[11] Patent Number: 6,007,811
[45] Date of Patent: Dec. 28, 1999

[54] METHOD OF PRODUCING FIBRIN SEALANT FROM CLOTTING FACTORS IN FISH BLOOD

[75] Inventors: Evelyn S. Sawyer; Philip J. Sawyer, both of Arundel, Me.; Jed B. Gorlin, Minneapolis, Minn.; Paul A. Jamney, Boston, Mass.

[73] Assignee: Sea Run Holdings, Inc., Arundel, Me.

[21] Appl. No.: 09/108,308

[22] Filed: Jul. 1, 1998

Related U.S. Application Data

[60] Provisional application No. 60/051,429, Jul. 1, 1997.
[51] Int. Cl.$^6$ .................................................. A61K 35/16
[52] U.S. Cl. .................... 424/94.64; 424/530; 424/529; 530/857; 530/380; 530/381; 530/382
[58] Field of Search ..................... 424/93.7, 530, 424/93.73, 529, 94.1, 94.64; 530/857, 380, 381, 382, 387; 735/2

[56] References Cited

U.S. PATENT DOCUMENTS 5,583,114  12/1996  Barrows et al. ........................ 514/21

OTHER PUBLICATIONS

T. Kurokawa et al., "Purification of flounder (*Paralichthys olivaceus*) fibronectin and its localization during re–epithelialization at a fin wound". *Journal of Fish Biology.* vol. 43, pp. 421–432, 1993.

K.J. Van VLIET et al., "A Thrombelastographic Study of the Effect of Stress on the Blood Coagulation in *Crypinus Carpio* (Cyprinidae) and *Oreochromis Mossambicus* (Cichlidae)". *Comp. Biochem. Physiol.* vol. 82A, No. 1, pp. 23–27, 1985.

Guy Hewlett, "Strategies for optimising serum–free media." *Cytotechnology.* vol. 5, pp. 3–14, 1991.

Russell F. Doolittle, "The Evolution of the Vertebrate Plasma Proteins". *Biol. Bull.* vol. 172, pp. 269–283, Jun. 1987.

Bullock, Gland Conroy DA, "Diseases of Fish Book 2A Bacterial Diseases of Fishes". Suieszko, S.F. and Axelrod H.R. Eds.) 1971, pp. 21–59, TFH Publications.

Russel F. Doolittle et al., "Species Differences in the Interaction of Thrombin and Fibrinogen". *Journal of Biological Chemistry.* vol. 237, No. 10, pp. 3123–3127, Oct. 1962.

K. Sandnes et al., "Normal ranges of some blood chemistry parameters in adult farmed Atlantic salmon, *Salmo salar*". *J. Fish Biol.* vol. 32, pp. 129–136, 1988.

Doolittle, Russell F., and Surgenor, Douglas M. "Blood Coagulation In Fish". American Journal of Physiology, vol. 203, No. 5, Nov., 1962, pp. 964–970.

Gibble, J.W., and Ness, P.M. "Fibrin glue: the perfect operative sealant?" Transfusion, vol. 30, No. 8, 1990, pp. 741–747.

Janmey, Paul A., et al. "Effects of Actin Filaments on Fibrin Clot Structure and Lysis". Blood, vol. 80, No. 4, Aug. 15, 1992, pp. 928–936.

Kawatzu Hiroshi and Kondo Kengo, "Prothrombin Time of Common Carp Blood", Nippon Suisan Gakkaishi, 55(1), 183, 1989.

Martinowitz, Uri and Saltz, Renato, "Fibrin sealant". Current Opinion in Hematology, 1996, vol. 3, pp. 395–402.

Ngai, Philip K. and Chang, Jui–Yoa, "Anovel one–step purification of human α–thrombin after direct activation of crude prothrombin enriched from plasma", Biochem. J. 1991, 280: pp. 805–808.

(List continued on next page.)

*Primary Examiner*—Jean C. Witz
*Attorney, Agent, or Firm*—Rabin & Champagne, P.C.

[57] ABSTRACT

The present invention is a fibrin sealant and a method for producing a fibrin sealant from fish blood. Whole blood is drawn from the donor fish and centifuged to separate blood cells from plasma. Prothrombin and fibrinogen are extracted from this plasma, and the prothrombin is activated to thrombin. The fibrinogen and thrombin components are then combined as needed to form the fibrin sealant.

18 Claims, 4 Drawing Sheets

OTHER PUBLICATIONS

Nichols, William L., "Adverse Antibody–Mediated Reactions to Topical Bovine Thrombin and Fibrin Glue." Fibrin Sealants; characteristics and clinical uses. Proc. of Conference. Bethesda, MD Dec. 8–9, 1994. pp. 5–10.

Silver, Frederick H., et al. "Preparation and use of fibrin glue in surgery". Biomaterials 1995, vol. 16, No. 12, pp. 891–903.

Smit, G.L. and Schoonbee, H.J. "Blood coagulation factors in the freshwater fish*Oreochromis mossambicus*". J. Fish Biol. 1988, 32:673–677.

Will, R.G., et al., "A new variant of Creutzfeldt–Jakob disease in the UK". The Lancet, vol. 347, Apr. 6, 1996, pp. 921–925.

1 = 100% Deformation

METHOD OF PRODUCING FIBRIN SEALANT FROM CLOTTING FACTORS IN FISH BLOOD

This application claims the benefit of U.S. Provisional Application No. 60/051,429, filed Jul. 1, 1997.

FIELD OF THE INVENTION

The present invention relates generally to hemostatic therapies useful in surgery and other medical applications to slow or stop bleeding. In particular, the present invention would replace conventional medical fibrin sealants made from human and bovine blood products with a sealant derived entirely or in part from fish blood.

BACKGROUND OF THE INVENTION

Fibrin sealants are well-established as effective hemostatic agents with numerous applications in cardiac, thoracic, plastic, and neurosurgery; skin grafting, repair of bony defects, and treatment of gastric ulcers (Gibble and Ness, 1990). The common denominator of these applications is the need for a biodegradable tissue sealant that serves to diminish bleeding or serosol leakage, or to provide additional strength to surgical anastamoses. Current fibrin sealants consist of human fibrinogen and Factor VIII derived from human plasma cryoprecipitate, and thrombin from bovine plasma (Martinowitz and Saltz, 1996). Outside the United States, commercially prepared fibrin glue kits are available which contain pasteurized human fibrinogen, bovine thrombin, and other ingredients. The FDA has not approved use of these kits due to concerns for efficacy and safety including possible viral disease risks. Therefore, U.S. surgeons frequently prepare homemade "glues". These consist of fibrinogen extracted from the patient's own plasma (autologous plasma), combined with bovine thrombin to form a glue mixture (Silver et al., 1995).

Problems with fibrin sealants now in use center on the possibility of disease transmission from both the human-derived fibrinogen from non-autologous sources, and the bovine thrombin. Recent experience in Britain linking bovine spongiform encephalopathy (BSE) and Creutzfelt-Jakob Disease in humans demonstrates the dangers of cross-mammalian infectious agents (Will et al., 1996). The dangers of viral infection from non-autologous human blood products is well known. Although various techniques are available to detect and inactivate human and other mammalian viruses, they offer relative safety only from known risks, and little if any protection from thermoresistant viruses or new infectious agents such as prions (Murphy, 1996). Also, an emerging problem with bovine thrombin is the development of antibodies to bovine blood proteins by some patients (Nichols, 1994).

The rapid clotting of blood from most teleosts (bony fish) is well-known. The mechanism is a cascade of clotting factors ending in the conversion of fibrinogen to fibrin by thrombin, similar to clotting in humans (Doolittle and Surgenor, 1962). However, these authors and others (Smit and Schoonbee, 1988; Kawatsu and Kondo, 1989) found many of the clotting proteins in fish to be species-specific. Clotting factors in fish have received little attention for human applications for several reasons. First, species-specificity of some fish plasma proteins pointed to a general incompatibility of fish and human blood proteins, discouraging further investigation. Second, only in the past few years have the dangers, both real and perceived, from human and bovine blood products been publicized. Third, until the recent establishment of commercial aquaculture, large quantities of aseptic blood of consistent composition and quality were not available.

SUMMARY OF THE INVENTION

It is therefore an object of the present invention to provide a fibrin sealant that minimizes the possibility of disease transmission.

It is a further object of the present invention to provide a method of producing a fibrin sealant from fish blood.

The present invention is a fibrin sealant and a method for producing a fibrin sealant from fish blood. Whole blood is drawn from the donor fish and centifuged to separate blood cells from plasma. Prothrombin and fibrinogen are extracted from this plasma, and the prothrombin is activated to thrombin. The fibrinogen and thrombin components are then combined as needed to form the fibrin sealant.

DETAILED DESCRIPTION OF THE INVENTION

We have found that the blood of farmed, domesticated stocks of coldwater fishes, especially the salmonids (salmon and trout), contains quantities of fibrinogen and thrombin similar to human blood, and these clotting factors can be extracted from salmonid blood by known methods. We have demonstrated that clots (fibrin sealants) made from polymerization of salmonid fibrinogen and thrombin, or salmonid fibrinogen and mammalian thrombin, have clot strength and elasticity (FIGS. 1 and 2), clotting times (FIG. 3), fibrinolytic characteristics, and adhesion to mammalian tissue similar to those of clots made with highly purified human fibrin.

Figure 4:
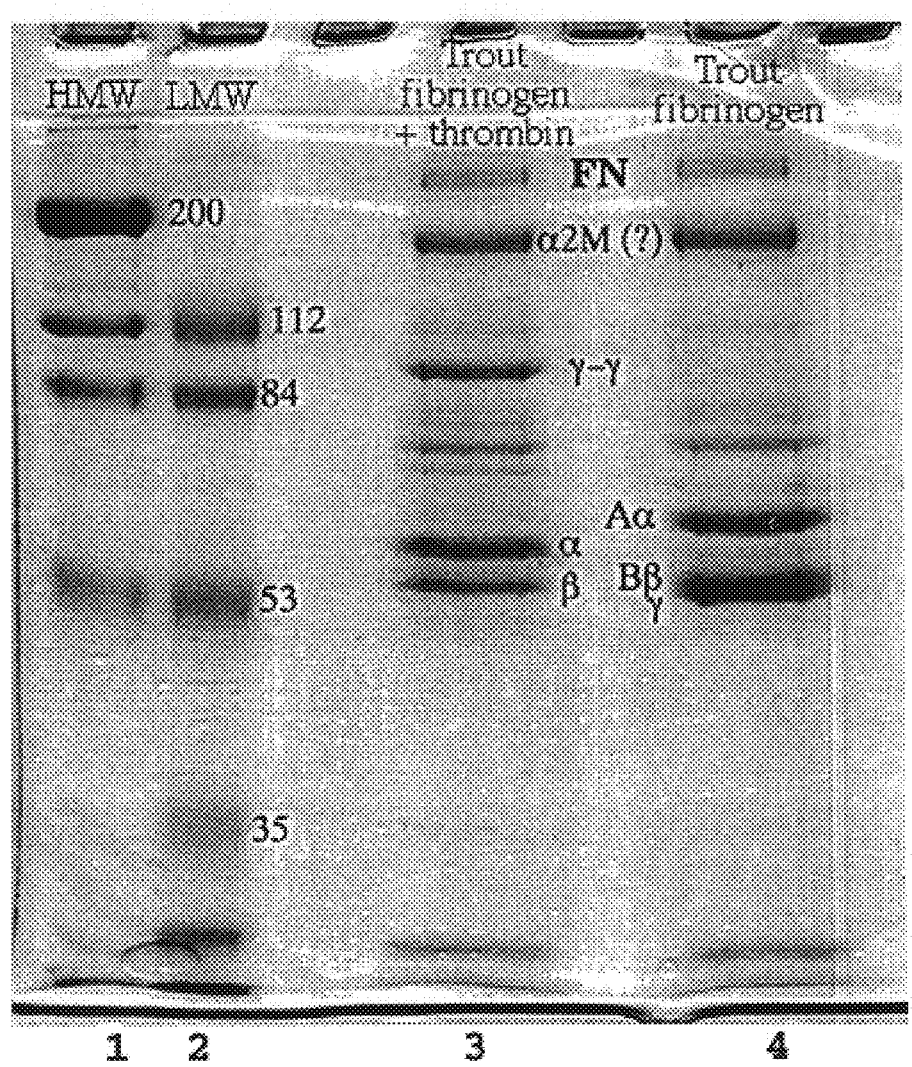
FIG. 4 shows conversion of trout fibrinogen to a crosslinked fibrin clot by bovine thrombin and endogenous Factor XIIIa.

All testing was performed with trout (*Oncorhynchus mykiss*) and/or salmon (*Salmo salar*) plasma or components. Although the only purified trout or salmon protein used was fibrinogen, we have demonstrated the efficiency of endogenous trout thrombin and Factor XIIIa (FIG. 4). Bovine thrombin was used for proof of concept and to demonstrate the compatibility of the fish and mammalian clotting factors.

A 2 mg/ml quantity of trout fibrinogen was clotted by addition of 1 unit/ml bovine thrombin and 1 mMCa2+ in excess of the 5 mM EDTA added to inhibit spontaneous plasma polymerization. The two left lanes show high (HMW, lane 1) and low (LMW, lane 2) molecular weight standards on a 10% SDS-polyacrylamide gel, along with the molecular weights (in 1000) of the standards. The three bands around 60 kDa in lane 4 are characteristic of the Aα, Bβ, and γ chains of fibrinogen. A higher molecular weight band corresponds to fibronectin (FN), an expected containment of fibrinogen preparations made by ammonium sulphate precipitation.

After addition of thrombin, there are several characteristics of changes typical of fibrin formation evident in lane 3.

First, the mobility of Aα and Bβ chains increases as the A and B peptides are cleaved by thrombin. Second, the band corresponding to the γ chain disappears, and another band at higher molecular weight corresponding to a covalently ligated γr dimer appears because of the activity of trout Factor XIIIa that copurifies with fibrinogen and is activated by thrombin. Polypeptides that are not part of fibrinogen are unaltered by thrombin.

Figure 1:
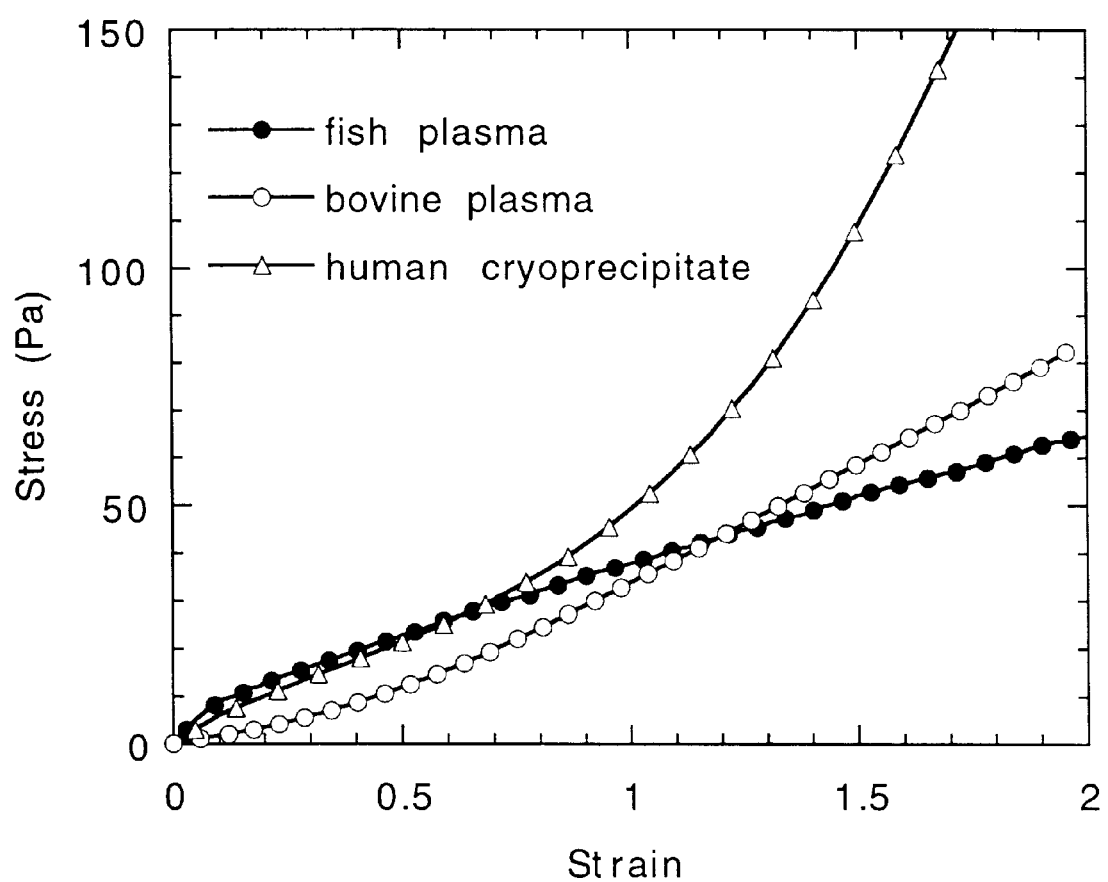
FIG. 1 shows the stress developed during continuous shear deformation of plasma clots adherent between two mouse skin surfaces.

The strength of the fish sealant is similar to that of the human-bovine product, as shown in FIG. 1. An important characteristic of fibrin gels is that they are strain-hardening; that is, they become stronger the more they are deformed up to a limit strain typically on the order of 100%. At 100% strain, the maximum clinically realistic level, fish, bovine, and human gels show similar characteristics when tested on mouse skin in a Rheometrics RFS-2 fluid spectrometer using standard methods (Janmey et al., 1992).

Adhesion to the mouse skin was equally strong with all three gels.

Figure 2:
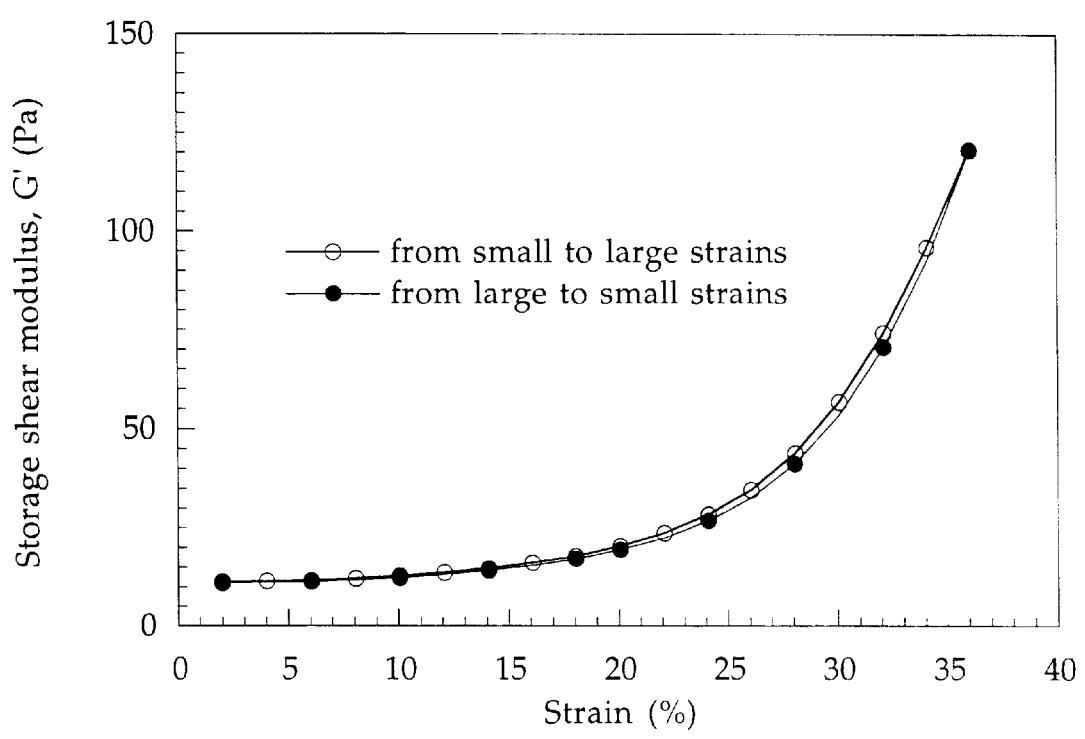
FIG. 2 shows a plot of storage shear modulus versus strain for fibrinogen purified from frozen salmon plasma.

FIG. 2 shows that salmonid fibrinogen polymerized by bovine thrombin forms clots (gels) with strain-hardening and nearly total elastic recovery after deformation that is characteristic of human fibrin gels.

Figure 3:
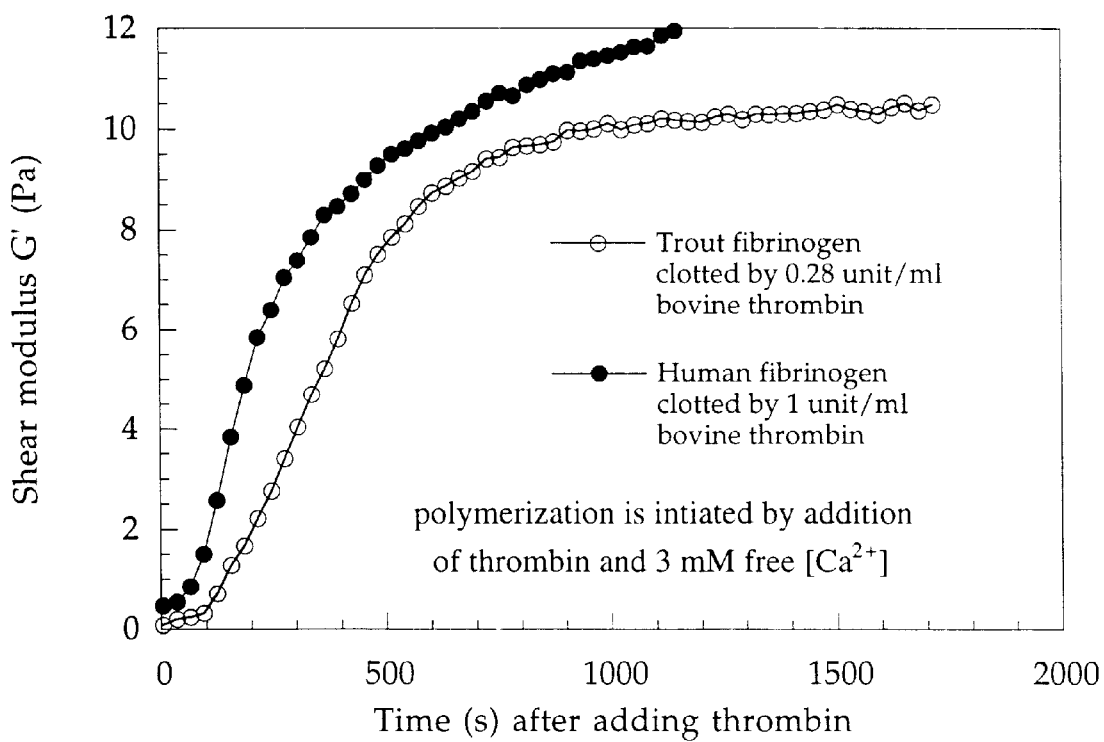
FIG. 3 shows clot characteristics of human and trout fibrinogens.

The elastic or shear modulus G2 (the ratio of stress to strain) of clots (gels) made with trout fibrinogen is compared in FIG. 3 with those made from human fibrinogen. Both show similar clotting times and result moduli in excess of 10 Pa (100 dynes/cm$^2$).

Fibrinolytic properties of the fish-derived gel were tested by adding human plasmin. When 0.3 U/ml human plasmin was added to 2.5 mg/ml trout fibrinogen, prior to the addition of thrombin, the solution did not clot, as shown by the absence of a measurable elastic modulus. When plasmin was added immediately after thrombin, polymerization occurred, but the clots were much weaker than control clots made without plasmin, and dissolved shortly after gelation. Therefore, trout fibrinogen is a suitable substrate for human plasmin, and concerns that its use could result in embolic or thrombotic complications are eliminated.

The advantages of the fish-derived substances include the following:

A. Safety

The safety advantages of deriving the components of a fibrin sealant, fibrinogen and thrombin, from salmonid blood can be best understood in the context of the evolutionary biology of these fish. The fishes as a group (phylum) are widely separated from mammals, and as such, their disease organisms have evolved on separate paths. These differences are exemplified in standard laboratory methods in which various fish cell lines must be used to propagate fish viruses, as mammalian cell lines are used for mammalian viruses (Wolfe, 1988). Another difference is temperature. In coldwater fish such as salmon or trout, their maximum body temperature is the same as the water in which they live— normally between about 0° C. and 18° C., a temperature range nearly 30° C. below that of humans or most other mammals. Therefore, these fish have few, if any, infectious agents that can survive in humans. These are just some of the manifestations of the wide evolutionary distance between fish and mammals that result in safety from infectious agents.

B. Control of Source

Clotting factors derived from human or bovine blood may be inconsistent in quality due to variations in both genetics and environment of the donors. In contrast, domesticated, farmed fish that serve as blood donors are well-defined as to diet, habitat, reproductive status, life history, and genetic background. The degree of control that aquaculture provides for these donor animals results in improved uniformity of product. Unlike autologous cryoprecipitate, pre-tested salmonid fibrinogen offers consistent concentrations and generally greater quality control.

C. Rapid Clotting Time

Clotting time (thrombin time) in salmon and trout plasma was measured by standard coagulation laboratory techniques using bovine thrombin. Compared to a Human Reference Range of 12–16 seconds, mean salmon thrombin time was 6.8 seconds and trout thrombin time was 7.1 seconds.

For applications requiring a fibrin sealant, the present invention, derived from fish, can be used with similar efficacy, and advantages in safety, quality control, and product content over the human/bovine-derived fibrin sealants currently in use.

The process begins with the consistent and reproducible conditions in which donor fish are reared. All fish used as plasma sources preferably are 1) progeny of domesticated brood stock; 2) inspected for fish disease under the protocols of the American Fisheries Society Blue Book; 3) 1 kg. or more in weight; 4) fed a commercially manufactured pelleted feed appropriate to the species; and 5) held in waters monitored and found free of environmental pollutants or toxins.

The coldwater fishes used as donors preferably are rainbow trout (*O. mykiss*) and Atlantic salmon (*S. salar*). These species are selected because they are reared in large numbers, and individuals grow large enough (over one kilogram) so that blood can be drawn easily. Other farmed cold-water fishes, such as halibut or cod, may be used as donor fish and might satisfy all the above criteria.

The fish are preferably starved for 24 hours to reduce handling stress. Fish are preferably anesthetized to a loss of reflex activity in a solution of tricane methane-sulfonate (MS-222) or in carbon dioxide bubbled through the water. Whole blood is then drawn from the caudal vein or artery of the fish by known methods such as using a needle and syringe, vacuum tube, or other vacuum device. With all of these devices, one part of a 1 M solution of sodium citrate is added to nine parts of whole blood as an anticoagulant.

The whole blood is held at about 1° C. to 4° C. for no more than about four hours before centrifugation. The separation of blood cells and plasma preferably is done at about 4° C. and at least about 1000 g for about ten minutes. The plasma may then be frozen, preferably at −20° C., or extracted immediately.

Extraction procedures are preferably known methods currently used for bovine thrombin and fibrinogen.

Extraction of prothrombin is preferably performed by first using a solution of barium chloride. One part of a 1 M solution of cold (4° C.) barium chloride is added to eleven parts plasma and stirred for about 30 minutes. The mixture is then centrifuged at about 3500 g for about 30 minutes and the pellet containing the prothrombin is frozen, preferably at −20° C. Activation of the prothrombin to thrombin and subsequent extraction methods are preferably carried out with the thawed prothrombin according to the methods of Ngai and Chang (1991).

Fibrinogen may be extracted from the supernatant using the ammonium sulfate methods described by Silver et al. (1995). One part of a saturated (4.5 M) solution of ammonium sulfate at about 4° C. is added to three parts of the supernatant. The mixture is centrifuged, preferably at about 14,000 g at about 4° C. for about 8 minutes.

The fibrinogen is resuspended in Tris buffered saline (pH 7.4) at room temperature at a concentration of 2.5 mg/ml. The thrombin is resolublized in 40 mM calcium chloride at a concentration of 0.25–1 NIH units/ml. Commerically available bovine or human thrombin may be used at similar concentrations with the fish fibrinogen to achieve similar results, but without the degree of safety provided by the fish thrombin.

The two components may be applied to the wound or leakage simultaneously using a commercially available double syringe or spray applicator.

What is claimed is:

1. A method of producing a fibrin sealant, comprising:
   drawing whole blood from donor fish;
   separating plasma from the whole blood;
   extracting fibrinogen from the plasma;
   extracting prothrombin from the plasma;
   activating the prothrombin to thrombin; and
   combining the thrombin and the fibrinogen to form the fibrin sealant.
2. The method of claim 1, wherein the donor fish are domesticated, farmed fish.
3. The method of claim 1, wherein the donor fish each weigh at least 1 kilogram.
4. The method of claim 1, further including starving the donor fish for about twenty-four hours prior to drawing whole blood from the donor fish.
5. The method of claim 1, wherein separating plasma from the whole blood is performed at about 4° C. and includes centrifugation at at least about 1000 g for about ten minutes.
6. The method of claim 1, further including adding calcium to the thrombin and the fibrinogen to form the fibrin sealant.
7. The method of claim 1, wherein the donor fish are coldwater fish.
8. The method of claim 1, wherein combining the thrombin and the fibrinogen includes applying the thrombin and the fibrinogen to mammalian tissue.
9. The method of claim 8, wherein the mammalian tissue is human tissue.
10. A method of producing a fibrin sealant, comprising:
    drawing whole blood from donor fish;
    separating plasma from the whole blood;
    extracting fibrinogen from the plasma; and
    combining mammalian thrombin with the fibrinogen to form the fibrin sealant.
11. The method of claim 10, further including adding calcium to the mammalian thrombin and the fibrinogen to form the fibrin sealant.
12. The method of claim 10, wherein the donor fish are coldwater fish.
13. The method of claim 12, wherein the donor fish are selected from the group of fish consisting of rainbow trout and Atlantic salmon.
14. The method of claim 10, wherein the mammalian thrombin is bovine thrombin.
15. The method of claim 10, wherein the mammalian thrombin is human thrombin.
16. The method of claim 10, wherein combining the mammalian thrombin and the fibrinogen includes applying the mammalian thrombin and the fibrinogen to mammalian tissue.
17. The method of claim 16, wherein the mammalian tissue is human tissue.
18. The method of claim 7, wherein the donor fish are selected from the group of fish consisting of rainbow trout and Atlantic salmon.

* * * * *